United States Patent
Chang et al.

(10) Patent No.: US 11,624,050 B2
(45) Date of Patent: Apr. 11, 2023

(54) MICRONEEDLE ARRAY ELECTROPORATION SYSTEM FOR CELL TRANSFECTION

(71) Applicant: THE BOARD OF REGENTS OF THE UNIVERSITY OF TEXAS SYSTEM, Austin, TX (US)

(72) Inventors: Lingqian Chang, Denton, TX (US); R. Lyle Hood, San Antonio, TX (US); Forhad Akhter, San Antonio, TX (US)

(73) Assignee: Board of Regents, The University of Texas System, Austin, TX (US)

(*) Notice: Subject to any disclaimer, the term of this patent is extended or adjusted under 35 U.S.C. 154(b) by 34 days.

(21) Appl. No.: 17/000,235

(22) Filed: Aug. 21, 2020

(65) Prior Publication Data

US 2021/0246408 A1 Aug. 12, 2021

Related U.S. Application Data

(60) Provisional application No. 62/890,030, filed on Aug. 21, 2019.

(51) Int. Cl.
*C12M 3/00* (2006.01)
*B01L 3/00* (2006.01)
*C12M 1/42* (2006.01)

(52) U.S. Cl.
CPC .................................. *C12M 35/02* (2013.01)

(58) Field of Classification Search
CPC ....... C12M 35/00; C12M 35/02; C12M 35/04
See application file for complete search history.

(56) References Cited

U.S. PATENT DOCUMENTS

| | | | | |
|---|---|---|---|---|
| 3,313,293 A * | 4/1967 | Chesebrough | ....... | A61N 1/0502 600/373 |
| 6,135,990 A * | 10/2000 | Heller | ................. | A61M 37/00 435/173.6 |
| 7,769,440 B2 * | 8/2010 | Hoff | ....................... | C12N 15/87 604/20 |
| 2008/0287857 A1 * | 11/2008 | Kjeken | .................. | A61N 1/327 604/21 |
| 2009/0030364 A1 * | 1/2009 | Harmon | ................ | A61N 1/327 604/21 |
| 2010/0204640 A1 * | 8/2010 | Mingozzi | ............... | A61N 1/327 604/21 |
| 2011/0009807 A1 * | 1/2011 | Kjeken | ................. | C12N 13/00 604/21 |
| 2014/0121587 A1 * | 5/2014 | Sallberg | ................ | A61N 1/306 604/21 |
| 2020/0261907 A1 * | 8/2020 | Xie | ........................ | G01N 27/02 |

OTHER PUBLICATIONS

Chang et al., "Controllable Large-Scale Transfection of Primary Mammalian Cardiomyocytes on a Nanochannel Array Platform" *Small* 2016, 12(43), 5971-5980.

(Continued)

*Primary Examiner* — Nathan A Bowers

(57) ABSTRACT

Disclosed is the design, fabrication, and characterization of a novel system comprising a parallel set of nanopore microneedles (NPMs) for cell transfection through controlled nanoelectroporation (NEP) and electrophoretic insertion of genetic materials.

16 Claims, 17 Drawing Sheets

(56) References Cited

OTHER PUBLICATIONS

Chang et al., "Magnetic Tweezers-Based 3D Microchannel Electroporation for High-Throughput Gene Transfection in Living Cells" *Small* 2015, 11(15), 1818-1828.

Gallego-Perez et al. "Topical tissue nano-transfection mediates non-viral stroma reprogramming and rescue" *Nature Nanotechnology* 2017, 12, 974-981.

Kotnik et al., "Sensitivity of transmembrane voltage induced by applied electric fields-a theoretical analysis" *Bioelectrochemistry and Bioenergetics* 1997, 43, 285-291.

Yang et al., "Exosomal transfer of miR-30a between cardiomyocytes regulates autophagy after hypoxia" J Mol Med 2016, 94, 711-724.

\* cited by examiner

Silica based hollow microneedle, Hexagonal Shape

MICRONEEDLE ARRAY ELECTROPORATION SYSTEM FOR CELL TRANSFECTION

CROSS REFERENCE TO RELATED APPLICATIONS

This application claims priority to U.S. Provisional Application Ser. No. 62/890,030 filed Aug. 21, 2020, entitled "Microneedle Array Electroporation System For Cell Transfection," the entire contents of which are hereby incorporated by reference.

BACKGROUND

While small capsized cargo can easily enter the cytosol of a cell by multiple means, larger drugs and plasmids face difficulties without the aid of membrane permeabilization. While many methods have been developed to facilitate transmembrane transport, most are hindered by either low efficiency or low throughput. Limited understanding of the complex mechanics in play and complicated interactions of the micro- and macro-environments provide obstacles to efficient and non-lethal bulk cell transfection. Herein, is described an invention that overcomes these obstacles through enabling nanoelectroporation to 3D cell volumes.

SUMMARY OF THE INVENTION

Disclosed herein is a device configured for controlled nanoelectroporation and/or electrophoretic insertion of genetic materials into cells, the device comprising: an array of microneedles, each microneedle comprising an elongated shaft having a sharp tip at its distal end, the shaft being formed from a continuous wall that defines an interior space inside the shaft, wherein the shaft comprises a plurality of nanopores that extend through the continuous wall and one or more electrodes that surround an outer surface of the shaft at one or more discrete locations along the length of the shaft, wherein each microneedle further comprises an insulated wire that extends along the shaft to each electrode, the one or more insulated wires being in electrical communication with the one or more electrodes.

Certain embodiments of the invention comprise a transdermal microneedle array with distributed nanochannels capable of reversibly electroporating cells for efficient transfection of genetic material and cell transformation. The needle geometries will allow transformation at depth and in three dimensions. The three-dimensional shape of the individual microneedles may vary, as may the shape of the array. In some embodiments the microneedles are cylindrical or hexagonal. The individual microneedles are hollow and allow intracellular delivery through electroporation of cells in contact with the nanopores and electrophoretic material transfer. The design may be adapted to also enable laser emission, which could aid in cell membrane poration and manipulation of local biotransport.

Certain embodiments of the invention are configured to allow transdermal cell transformation at a depth dictated by the microneedle length. This could also be used to deliver immunogenic or genetic manipulators. Thus, it's a platform with a multitude of applications, including vaccine delivery, autograft development, skin lesion treatment, cosmetic treatment, cellular manufacturing, cellular regeneration, cancer treatment, scar removal, etc.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

Figure 1:
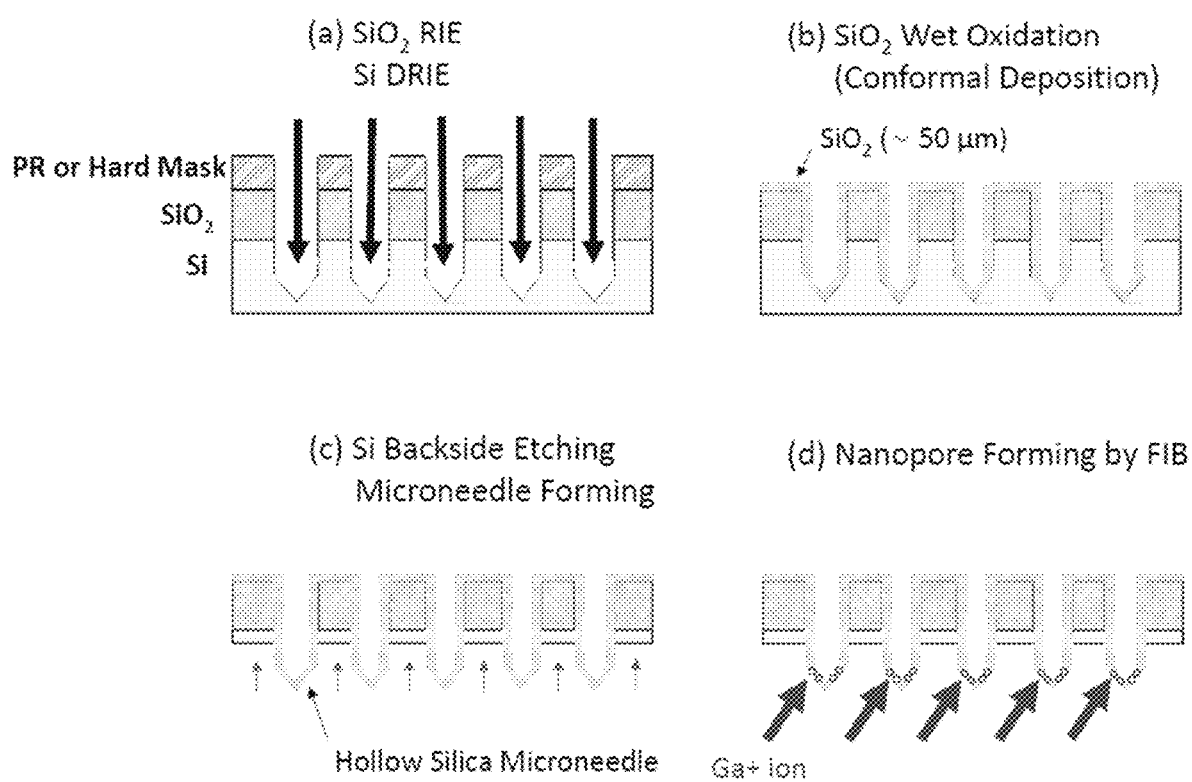
FIG. 1 illustrates NPM Fabrication.

As described above, systems and methods are needed for controlled nanoelectroporation (NEP) and electrophoretic insertion of genetic materials into cells. An application for the disclosed invention is to allow transdermal cell transformation at a depth dictated by the microneedle length. In certain embodiments a micro needle can be long, e.g., 5 mm, or short, e.g., 0.5, or any length there between (1, 1.5, 2, 2.5, 3, 3.5, 40, 4.5 mm). The disclosed invention may also be used to deliver immunogenic agents, genetic manipulators, or any other molecule capable of passage through the induced nanopores. The disclosed invention is a platform technology with a multitude of applications, including vaccine delivery, autograft development, skin lesion treatment, cosmetic treatment, cellular manufacturing, cellular regeneration, cancer treatment, and scar removal. Disclosed herein are examples of such systems and methods. In one embodiment, a system comprises a silicon microneedle array. In some embodiments the microneedle array is comprised of a plurality of hollow microneedles, each individual microneedle being 0.5 to 5 mm in length, 0.2 to 1 mm in diameter, and tapering to a sharp, sub 10 µm tip. In some embodiments each microneedle contains a plurality of 5 to 200 nm in diameter nanopores.

In the following disclosure, various specific embodiments are described. It is to be understood that those embodiments are example implementations of the disclosed inventions and that alternative embodiments are possible, including "hybrid" embodiments that include features of one or more different embodiments. All such embodiments are intended to fall within the scope of this disclosure.

Small capsized molecules, such as glucose or insulin, can readily access the cytosol through membrane transport or endocytosis. In contrast, many larger molecules and transcription plasmids encounter substantial difficulty being internalized without an exterior driving/permeabilizing force or agent (2-5). The transfection technology currently available is typically insufficient in efficiency (% of targeted population transfected), clinical safety, or throughput (transfection count per time). Viral transfection methods can achieve high transfection efficiency, but have long been associated with concerns about oncogenesis and clinical safety (6, 7). Efforts with chemical vectors, such as lipoplex (e.g. liposome) and polyplex (e.g. dendrimers), function through inducing endocytosis, a stochastic and slow procedure accompanied with low efficiency (<10%) for larger molecules (>6 kbps or 222 kDa) (8-11). Worse, many chemical vectors have been recognized to cause issues in vivo, such as immunogenic complications, multi-drug resistance, or unacceptable long circulating half-lives (12-14).

Physical methods, such as microneedles, biolistics, ultrasonic cavitation, and electroporation, have shown promise for in vivo transfection (15-26). Innovative micro-/nanoneedle patches have shown advantages in pain-free gene/drug delivery and controlled release. However, the distal needle tips only access the extracellular matrix (ECM), relying on endogenous uptake mechanisms to reach intracellular spaces (27-30). Therefore, cargo is limited to permeable drugs (e.g. insulin) that can be easily taken-up by cells (15, 31), or requires additional chemical permeabilizing agents with limitations as previously described. Biolistics (also known as gene gun transfection) deliver exogenous genetic material to the intracellular space though ballistic propulsion of DNA coated elemental particles. The approach suffers from random distributions of genetic material and irreversible damage to a sub-population of target cells (32). Bulk electroporation (BEP) typically confines millions of cells within a volume exposed to a high voltage (kVs) electric field pulsed between electrodes. Benefits of BEP include simple settings and high throughput. However, the entry of cargo relies on random molecular diffusion, which encounters exponentially decreasing efficiency with larger molecules (33-35). Studies have shown conventional electroporation for transdermal gene delivery in vivo resulted in low efficiency (<1%), but also caused substantial burns (36).

Previous research by Lingqian Chang et al. demonstrated that by directly abutting cells to a nanochannel (100-400 nm in diameter) and creating a local electric field, unique nanoelectroporation (NEP) can be achieved (1, 37-39). This approach was capable of electrotransfecting cells with: (1) dose control; (2) single-cell uniformity; (3) high delivery efficiency (>95%); (4) high cell viability (approaching 100%) for single cell gene transfection (37). A pulsed electric field applied across the nanochannel can accurately focus on the cell membrane, permeabilizing a small section. That same electric field can induce electrophoresis on charged molecules, such as plasmids or drugs, within the nanochannel, propelling them into the cytosol through local membrane disruption. A 3D array with hundreds of thousands of parallel nanochannels was fabricated on a silicon chip, enabling massive parallel transfection of cells in a single NEP event lasting milliseconds (37). Numerical studies by the same group indicated that NEP can precisely confine electroporation in an area of less than 200 nm on the cell membrane, causing negligible electrical stimulation to the greater cell (39). The performance characteristics of reasonable dosage control, single-cell uniformity, high efficiency transfection, and high post-transfection cell viability have been validated in a variety of cell types, including induced pluripotent stem cells (40), induced neurons (38), CAR-T cells (41), glioma stem cells (42), and cardiomyocytes (43). In a particularly interesting recent study published in Nature Nanotechnology, Gallego-Perez et al. showed that NEP could be employed for cell reprogramming: even beyond the NEP transfection boundary (3). Additional analysis attributed this distributed genetic reprogramming of naïve, non-electroporated cells to exosomes carrying the delivered genetic manipulation factors (Etv2, Foxc2, and Fli1). However, any circulating effect on naïve cells seemed to be limited to within a millimeter of the transfection site (3)

The fiberoptic microneedle device (FMD) is a sharp microneedle catheter capable of penetrating soft tissues and co-delivering laser light and fluid agents. The FMD was adapted to enhance the volumetric dispersal of macromolecules delivered to the brain through convection-enhanced delivery (CED) by concurrent delivery of sub-lethal photothermal hyperthermia (44-47). CED is a method of delivering chemotherapy to brain tumors through direct cannulation, avoiding obstacles to systemic drug circulation caused by the blood-brain barrier. For this, FMDs were stereotactically inserted symmetrically into both cerebral hemispheres of anesthetized rats to a depth of 1.5 mm. Laser irradiation (1,064 nm wavelength) at 0 (control), 100, and 200 mW was administered concurrently with CED infusions of liposomal rhodamine (LR) or gadolinium-Evans blueserum albumin conjugated complex (Gd-EBA) at a flow rate of 0.1 µl/min for 1 hour. These 100 and 200 mW irradiation intensities were identified in previous work to bound the threshold for photothermal damage in rat cerebral tissue. Line pressures were monitored during the infusions. ANOVA analyses demonstrated that co-delivery enhanced volumetric dispersal significantly, with measured volumes of $15.8\pm0.6$ mm$^3$ for 100 mW compared to $10.0\pm0.4$ mm$^3$ for its fluid only control and $18.0\pm0.3$ mm$^3$ for 200 mW compared to $10.3\pm0.7$ mm$^3$ for its fluid only control. Brains treated with 200 mW co-delivery exhibited thermal lesions, while 100 mW co-deliveries were associated with preservation of brain cytoarchitecture. These results demonstrated that both lethal and sub-lethal photothermal hyperthermia substantially increase the rate of volumetric dispersal in a 1 hour CED infusion.

In some embodiments single nanopore microneedles are arranged into parallel arrays. In some embodiments the microneedles have lengths from 300-3000 µm, microneedle bases between 500-1000 µm, various taper angles to a sharp tip, nanopore diameters from 50-500 nm, and nanopore densities from 50,000-50,000,000/cm$^2$. In some embodiments potential drops from 0.1-10,000 V and at frequencies from 0.1-1000 kHz are created across the individual nanopores. The system parameters in some embodiments are set at: cell size D is set to 10 µm, 1 to 13 µm (average nanopore length), R to 50 µm and w to 650 nm. In some embodiments parameters are taken from Kotnik et al., including extracellular fluid (phosphate buffered saline, PBS) and cytosol conductivities are 0.8 S m$^{-1}$ and 0.2 S m$^{-}$, respectively (62). The plasma membrane is may be 5 nm thick with a conductivity of $5\times10^{-7}$ S m$^{-1}$. The governing equation for the system (static electric field) used is: $\nabla(\sigma\nabla V)=0$, where σ is the conductivity and V is voltage.

NPM Fabrication: In some embodiments, a fabrication process for an array of hollow microneedles with patterned nanopores may use microfabrication techniques including photolithography, focused ion beam (FIB), and reactive ion etching (RIE).

An example fabrication approach is shown in FIG. 1. FIG. 1(a) shows that initial RIE and DRIE produces microneedle shapes between gaps in photoresist (PR) or hard mask layer; FIG. 1(b) shows that wet oxidation creates oxide layer; FIG. 1(c) shows that backside etching exposes microneedle lengths, and FIG. 1(d) shows that FIB creates nanopores.

To fabricate a parallel set of silica microneedles (e.g. 5×5) with lengths of 50-5000 μm tapered to a base of 0.1-3 mm in diameter, a p-type <100> single-crystalline silicon (Si) wafer may be employed as substrate. Thermal oxidation to create a thin layer of $SiO_2$ (1 μm) may be followed by lithographic patterning and RIE. The circular deep holes may be etched into the Si substrate by an anisotropic deep RIE (DRIE) process. Either a photoresist (e.g., SU-8) or thin-film metal (hard mask) may be used as an etching mask for both ME and DRIE steps. Next, the backside of the silicon wafer may be etched out, thus leaving the hollow silica microneedle structures. Electrodeposition may pattern an Au electrode layer (e.g. 1-100 nm) at the wafer's base and along the microneedles' lengths with multiple bands. Lastly, a high-energy Ga+ ion beam (FIB) may be employed to pattern nanopores within the microneedle wall.

Figure 2:
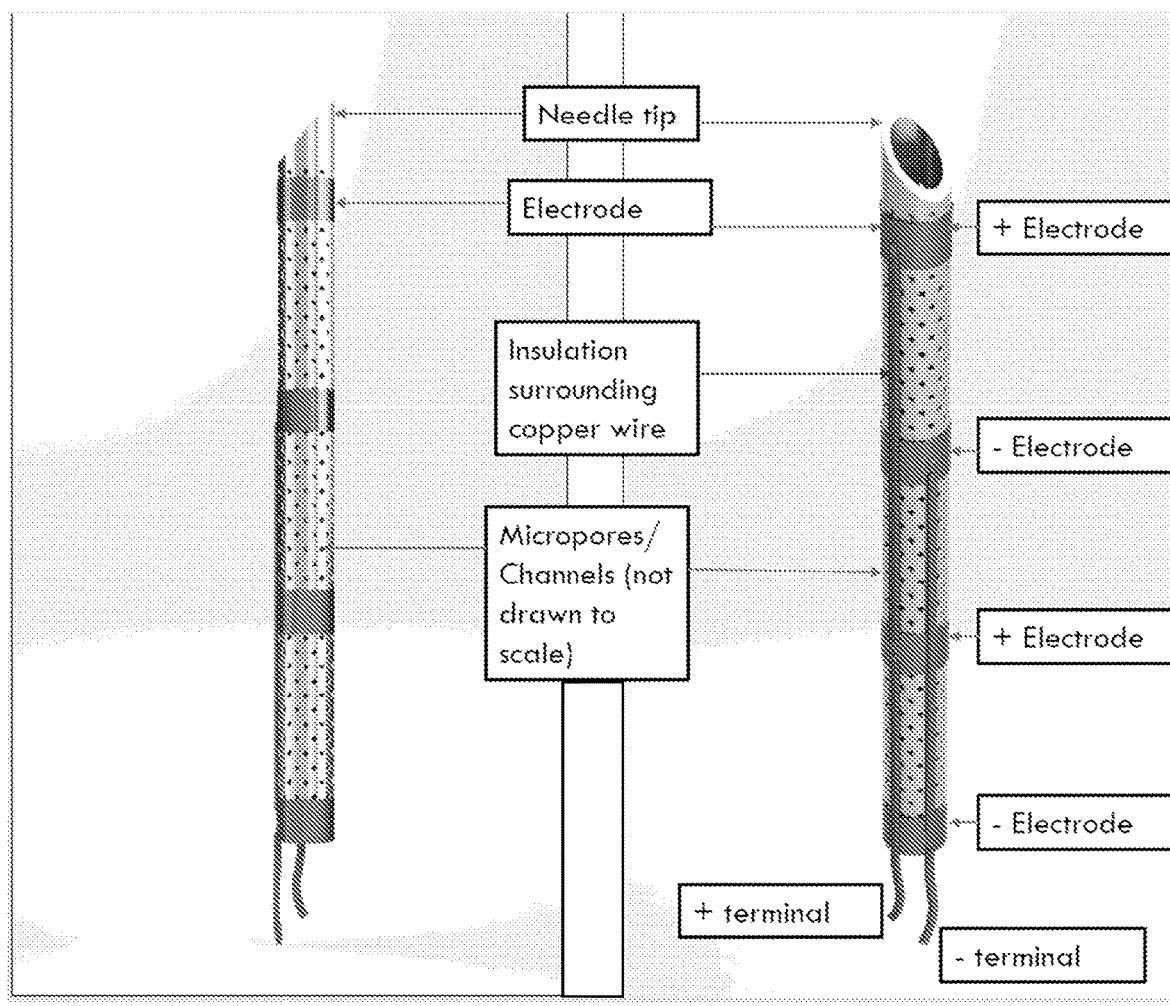
FIG. 2 is a cross-section view of a microneedle and its corresponding microholes.

FIG. 2 illustrates the distal tip of a single NPM. In some embodiments the NPM base may terminate in a flat plate or longer needle depending on manufacturing method. FIG. 2 is not to scale, the nanopores enlarged for clarity.

Figure 3:
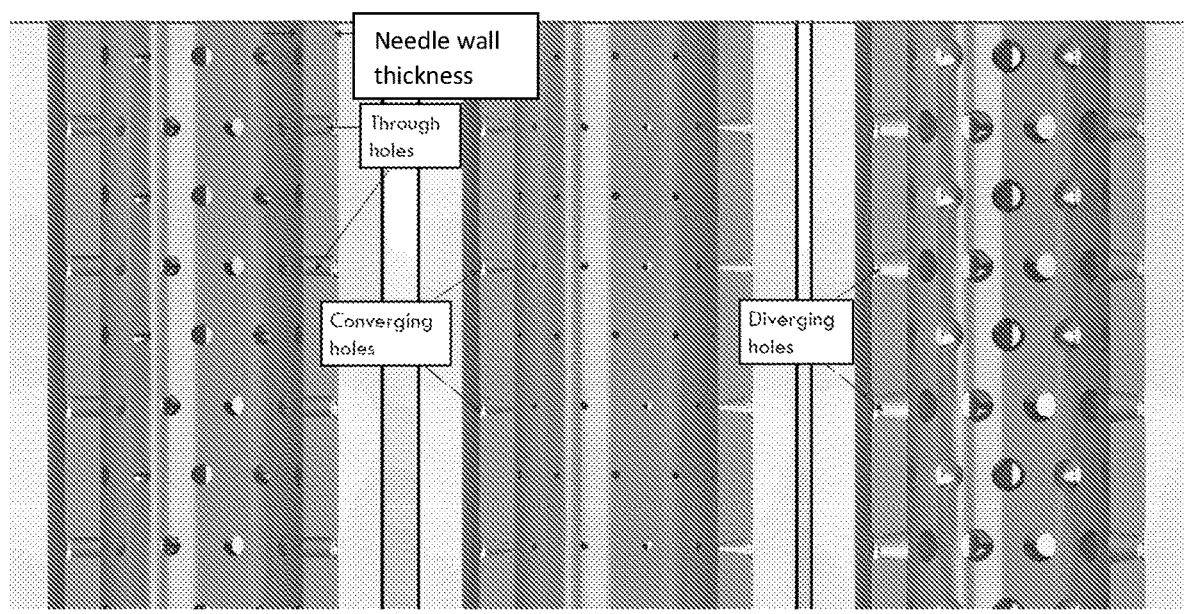
FIG. 3 illustrates various nanopore configurations

In some embodiments of the invention optimization of the various geometric contributions from the microneedle, electrodes, and nanopores towards the electric field generation and associated electrophoretic transport capabilities at both the local nanopore and macro (bulk electroporation) population levels. FIG. 3 illustrates various nanopore configurations.

In some embodiments groups of identical NPMs can be fabricated simultaneously through a combination of deep reactive ion etching (D-RIE) and focused ion beam (FIB) track generation. In some embodiments single NPMs may be fabricated through a variety of means. In some embodiments nanopores may be parallel, converging, or diverging in their intrawall geometry.

In some embodiments Cylindrical NPM geometries and complex electrode integration may provide advantages in electric field control and local electroporation capabilities relative to previous planar nanopore chip NEP designs.

In some embodiments repeatable transmembrane dosage control may be achievable through pulse magnitude and repetition with the NPM in H9C2 cells in vitro.

Example 1. H9c2 cells are trypsinized and loaded onto the NPM for 4 hours. Within this culture time, living cells will attach to the microneedle surface. A vacuum is applied through the nanopores during cell loading in order to enhance cell-to-nanopore contact. The vacuum effect through the nanopores is safe for the cells due to the high flow resistivity (37). After NEP, cells are trypsinized and transferred to cell culture flasks. Cell viability is determined by live/dead assay, and transfection efficiency is assessed through optical and fluorescent microscopy.

Exosome analysis is conducted similar to the methods described by Yang et al. (74). Briefly, trypsinized cells in culture media medium is centrifuged at 3000×G for 15 min to remove cells and cell debris. The supernatant is further concentrated by centrifugation for 30 min at 5000×g in a pre-rinsed centrifugal filter device (Amicon ultra-15). The samples are mixed with ExoQuick-TC reagent by vortexing, incubated overnight, and then centrifuged at 1500×g for 30 min at 4° C. to obtain the pellet. Pellets are resuspended in nuclease-free water. Fluorescence-activated cell sorting (FACS) is used to detect CD63, a surface marker expressed on exosomes. Exosomes from serum and H9c2 cells are absorbed onto 4-μM aldehyde/sulfate latex beads (Invitrogen) and incubated with anti-CD63 antibodies (Becton-Dickenson) followed by the secondary antibody anti-Mouse IgG (H+L), F(ab')2 Fragment (Cell Signaling Technology), before being washed and quantified via a FACS scan. PmaxGFP levels in exosomes are quantified through Real-time PCR via the SYBR® Premix Ex TaqIIKit (Takara).

Cell Transfection and Exosome Expression in 3D Hydrogel Culture: For these experiments, H9c2 cells (10^6) are seeded onto PEG-fibrinogen hydrogels (5×5×1 cm rectangular prism) immersed in DMEM with 10% FBS and incubated at 37 Celsius for 24 hours. Next, an NPM is advanced into the hydrogel, placing nanopores in direct contact with cells along the microneedle lengths. Voltage parameters disclosed above are used for NEP. Transfection outcomes are validated by delivering PI and PmaxGFP and inspected via assays and microscopy as previously described. Core samples of hydrogel are with biopsy needles at millimeter increments away from the NPM NEP sites. Once centrifuged to remove cell and hydrogel debris, exosomes are quantified as described previously.

In some embodiments the NPMs are capable of controlled electrophoretic transport both in general and for cell transfection. In some embodiments repeatable transmembrane dosage control is achievable through pulse magnitude and repetition with the NPM. Cell may be identified beyond the NEP transfection boundaries. Lastly, analysis of captured exosomes may show transport of PmaxGFP.

In some embodiments, to increase mechanical robustness, an elastomeric layer surrounding the microneedles along their length to provide lateral support and compress during insertion may be used (49).

In some embodiments multiple NPMs in parallel enable synergistic electroporation effects, such as bulk electroporation within the space between, to access a broader transfection volume beyond the simple additive volume per NPM.

In some embodiments multiple NPMs in parallel will induce heightened exosome production beyond the simple additive production per NPM.

In some embodiments employment of multiple NPMs in parallel will enable the simultaneous electrotransfection of multiple cell-types in co-culture.

Figure 4:
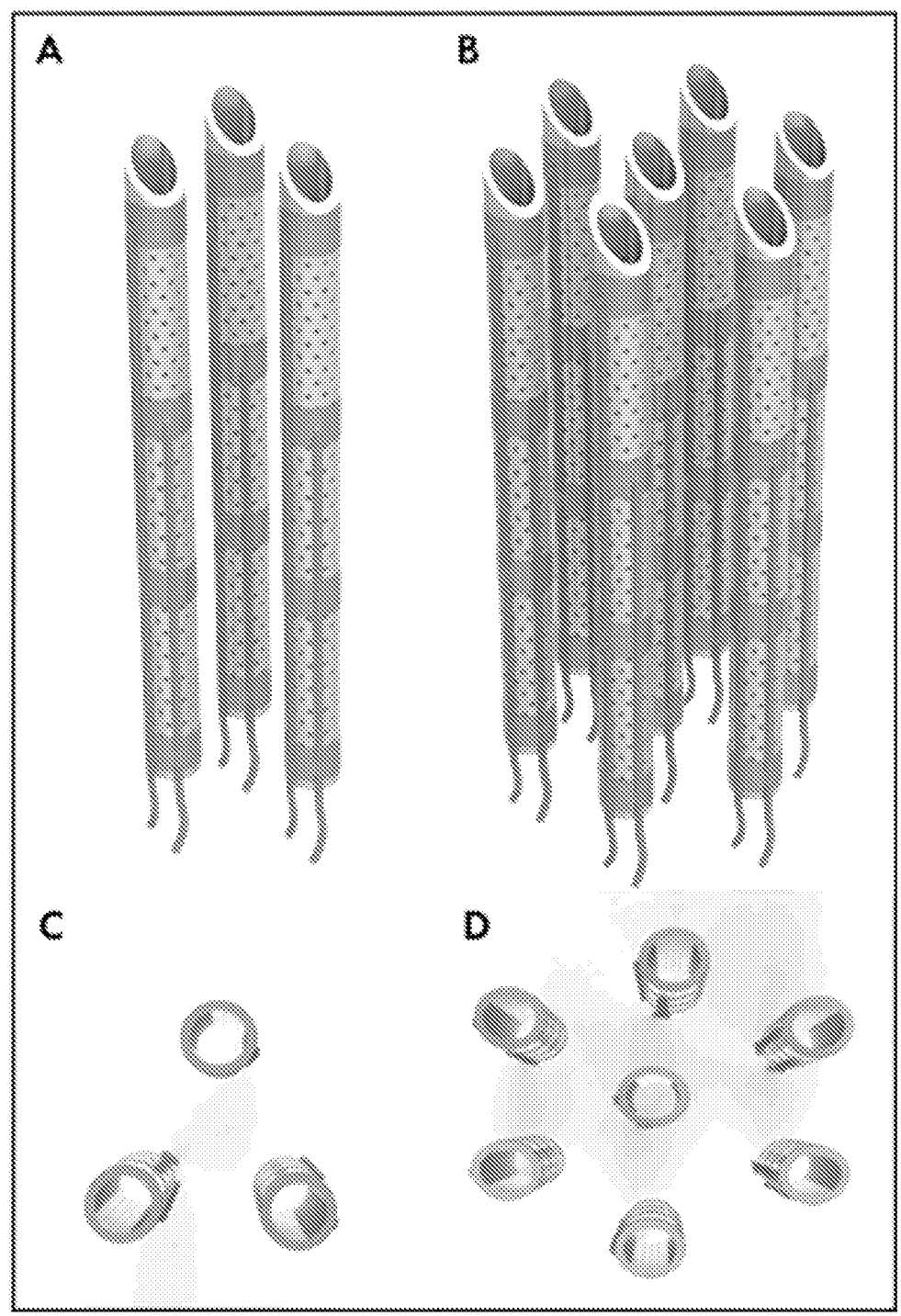
FIG. 4 illustrates various arrays of microneedles.

In some embodiments electrophoretic transport capabilities of parallel NPM arrays will have a synergistic effect beyond the additive. Two parallel NPM arrays are shown in FIG. 4, exhibiting both a triangular and hexagonal packing. Lateral FIG. 4(A) and top FIG. 4(C) views of triangular NPM array are shown. Lateral FIG. 4(B) and top FIG. 4(D) views of a hexagonal NPM array are shown. Pore sizes are not to scale.

Example 2. Cell Transfection and Exosome Expression in 3D Hydrogel Monoculture: H9c2 cells (10^6) are seeded onto PEG-fibrinogen hydrogels (5×5×1 cm rectangular prism) immersed in DMEM with 10% FBS and incubated at 37 Celsius for 24 hours. In addition, a secondary set of experiments with C2C12 myoblasts is conducted following the same protocol to establish baselines. Similar to previous, NPM arrays are advanced into the hydrogel, placing nanopores in direct contact with cells along the microneedle lengths. Voltage parameters as disclosed above are employed. Core samples of hydrogel are taken with biopsy needles at millimeter increments away from the NPM NEP sites. Transfection outcomes and exosome generation are assessed by delivering PI and PmaxGFP and inspected via assays, microscopy, FACS, and Real-Time PCR as previously described.

Cell Transfection in 3D Hydrogel Co-Culture: H9c2 (5×10^5) and C2C12 (5×10^5) cells are seeded onto PEG-fibrinogen hydrogels of various geometries and in various layer configurations while immersed in culture media. In some setups the cells freely intermix and have separate hydrogel layers seeded with the different cells and are stacked immediately prior to NEP via the NPM arrays. Voltage parameters disclosed above are employed. Core samples of hydrogel are taken with biopsy needles at millimeter increments away from the NPM NEP sites. Transfection outcomes and exosome generation are assessed by delivering PI and PmaxGFP and inspected via assays, microscopy, FACS, and Real-Time PCR as previously described.

In some embodiments the invention enables electroporation to be greater than additive due to induction of bulk electroporation between the microneedles. In some embodiments the invention enables synergistic enhancement beyond additive contributions due to exosome production and transfection beyond the NEP boundaries. In some embodiments the NPM will enable controlled transfection of multiple cell types simultaneously, which has significant potential in cell-based manufacturing of local small molecule and protein therapies.

In some embodiments the invention the device may include cylindrical microneedles: A silicon needle array with needles 0.5-5 mm in length, 0.2-1 mm in diameter tapering to a sharp, sub 10 µm tip, and with distributing 5-200 nm in diameter pores.

Some embodiments of the invention include hexagonal or circular microneedles. The microneedles can be hollow or solid. Microneedle shape may be modified to hexagonal structure for easy fabrication process. In one embodiment each side of the hexagon are equal length (0.1 to 1 mm) and taper to a sharp, 10 µm tip. In one embodiment the overall length of the needle would be 0.5 to 5 mm, with 5 to 200 nm diameter pores distributed on each face of the tapered hexagonal structure.

In some embodiments the tip of the microneedles may be optionally coated with gold that would be connected to a common terminal (+) so that these tips would work as cathode. The bottom surface of the base to which microneedles are attached may be coated with gold and connected to another terminal (−) to act as anode. Controlled electric pulse will be applied between these two terminals (+/−).

In some embodiments a separate gold wire (~10 to 50 µm diameter) will be used to travel right above the tips of the microneedles (uncoated). These wires will be connected to a common terminal and act as cathode. The anode will be the coated base.

This disclosed device may be constructed using cleanroom-based, nano-electro-mechanical system (NEMS) fabrication approaches (e.g. dry and wet etched, deep reative ion etching, electron beam lithography, etc.)

In various embodiments, microneedle designs, including, but not limited to those depicted in FIG. 2, 5, 8, 10, 11, 13, 16, or 17 can be configured into an array including but not limited to those depicted in FIG. 6, 7, 9, 12, 14, or 15.

Figure 5:
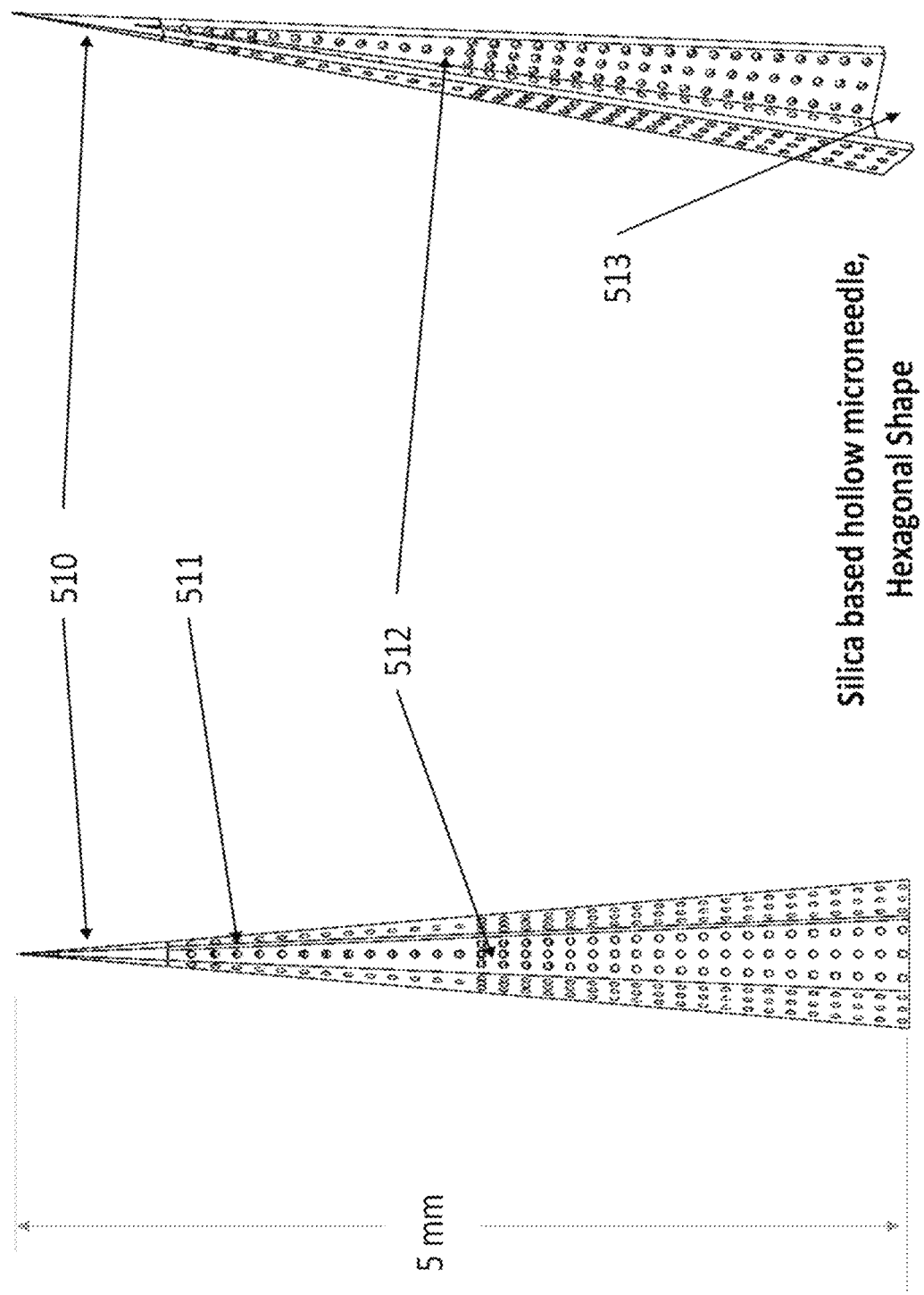
FIG. 5 illustrates a hollow microneedle, hexagonal in shape.

FIG. 5 illustrates one embodiment that is hexagonal hollow microneedle. This microneedle configuration has a gold coated tip (cathode) 510, a gold wire at the edge connected between the tip and cathode terminal 511, a plurality of nanopores 512 (5 to 200 nm diameter, not drawn to the scale) on the surface of hollow microneedle, a hollow structure to store fluid for electroporation 513.

Figure 6:
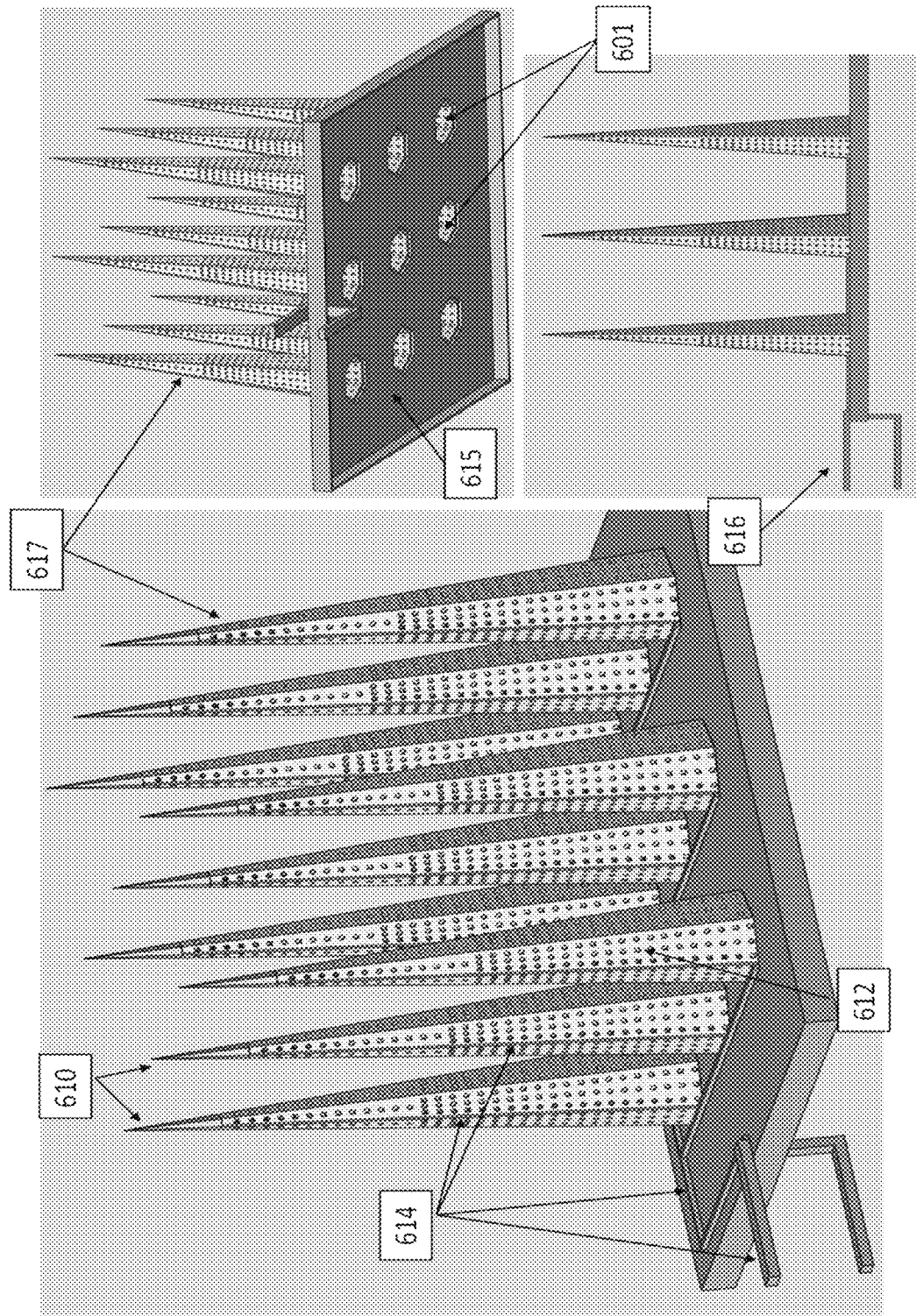
FIG. 6 illustrates an array of long hollow hexagonal microneedles.
Figure 7:
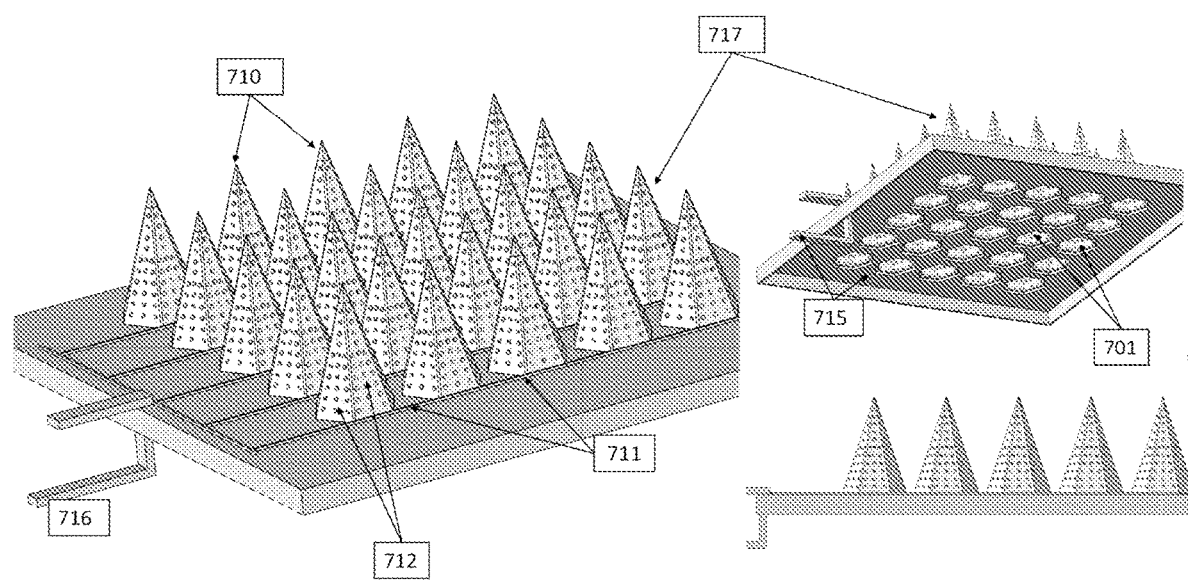
FIG. 7 illustrates an array of short hollow hexagonal microneedles.

The microneedles can be incorporated into an array that is supported on a base. The array is configured to have a cathode terminal and a anode terminal. The cathode terminal being in electrical communication with the tip of the microneedle and the anode terminal being in electrical communication with the array base. The tip and the base can be coated with a conducting material such as gold. FIG. 6 illustrates a long hexagonal hollow microneedle array 617. The hollow microneedles 601 having an optional gold coated microneedle tip (cathode) 610, a gold lining at the edge attached to the tip and a common terminal (+) 614, a plurality of nanopores (5-200 nm, not drawn to the scale) on the surface of hollow hexagonal microneedles (5 mm long) 612, a gold coated bottom chamber (anode, fluid reservoir) 615, and anode and cathode terminals 616 configured to produce electric pulses in the microneedle when in use. FIG. 7 illustrate a short hexagonal microneedle array 717 having hollow microneedles 701, a gold coated microneedle tip (cathode) 710, a gold lining at the edge attached to a common terminal (+) 711, a plurality of nanopores (5 to 200 nm, not drawn to the scale) on the surface of hollow hexagonal microneedles (0.5 mm long) 712, and the anode and cathode terminals 716.

Figure 8:
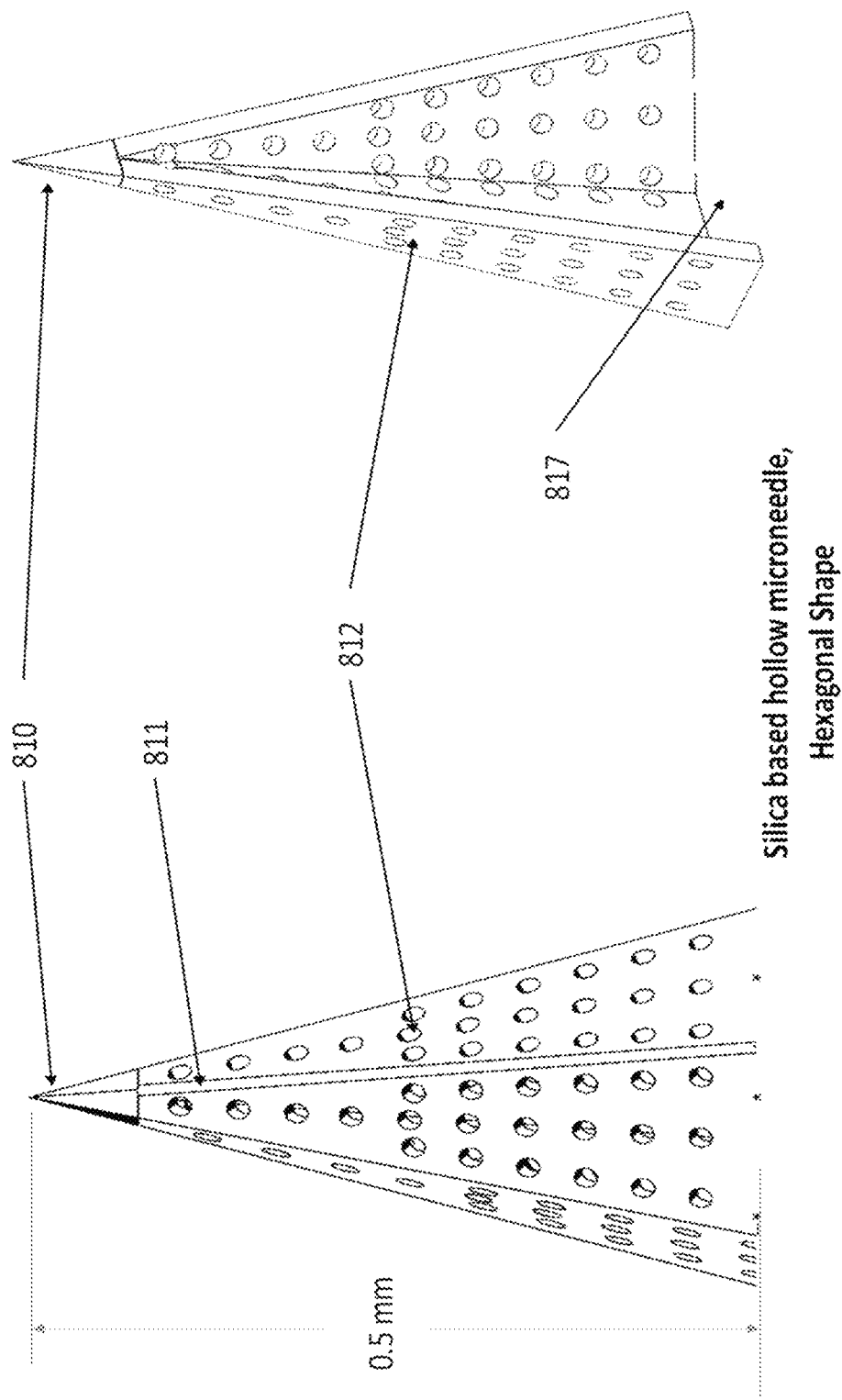
FIG. 8 illustrates a short hexagonal, hollow microneedle with a gold tip.

FIG. 8 illustrates one example of a short microneedle having a gold coated tip (cathode) 810, a gold wire at the edge connected between the tip and +terminal 811, a plurality of nanopores (5-200 nm diameter, not drawn to the scale) on the surface of hollow microneedle 812, and a hollow structure to store fluid inside for electroporation 817.

Figure 9:
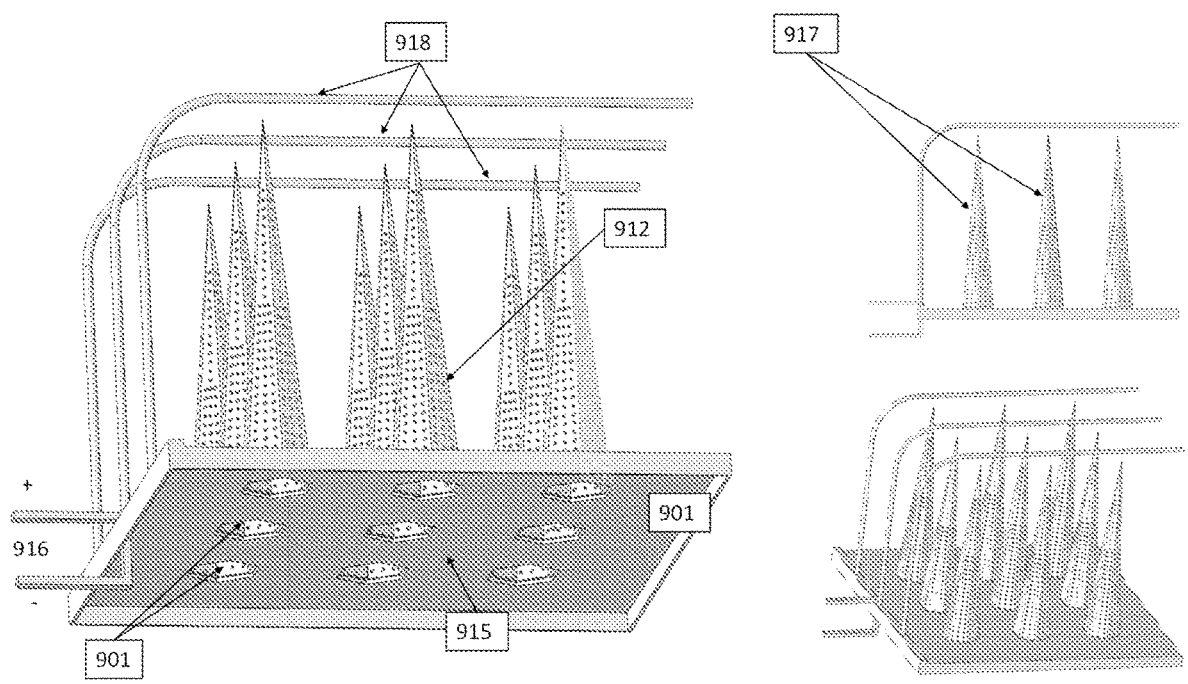
FIG. 9 illustrates an array with hexagonal hollow microneedles with external gold wiring above the tip of the microneedles, and nanopores on the surface.

FIG. 9 illustrates an array of hexagonal hollow microneedle 917 with an external gold wiring above the tip of the microneedles (cathode) 918. The array includes long or short hexagonal microneedles having a plurality of nanopores (5 to 200 nm, not drawn to the scale) on the surface of the hollow hexagonal microneedles (0.5 to 5 mm long) 912, a hollow microneedle bottom attached to the chamber 901, a gold coated bottom chamber (anode, fluid reservoir) 915, and an anode and cathode terminals 916.

Figure 10:
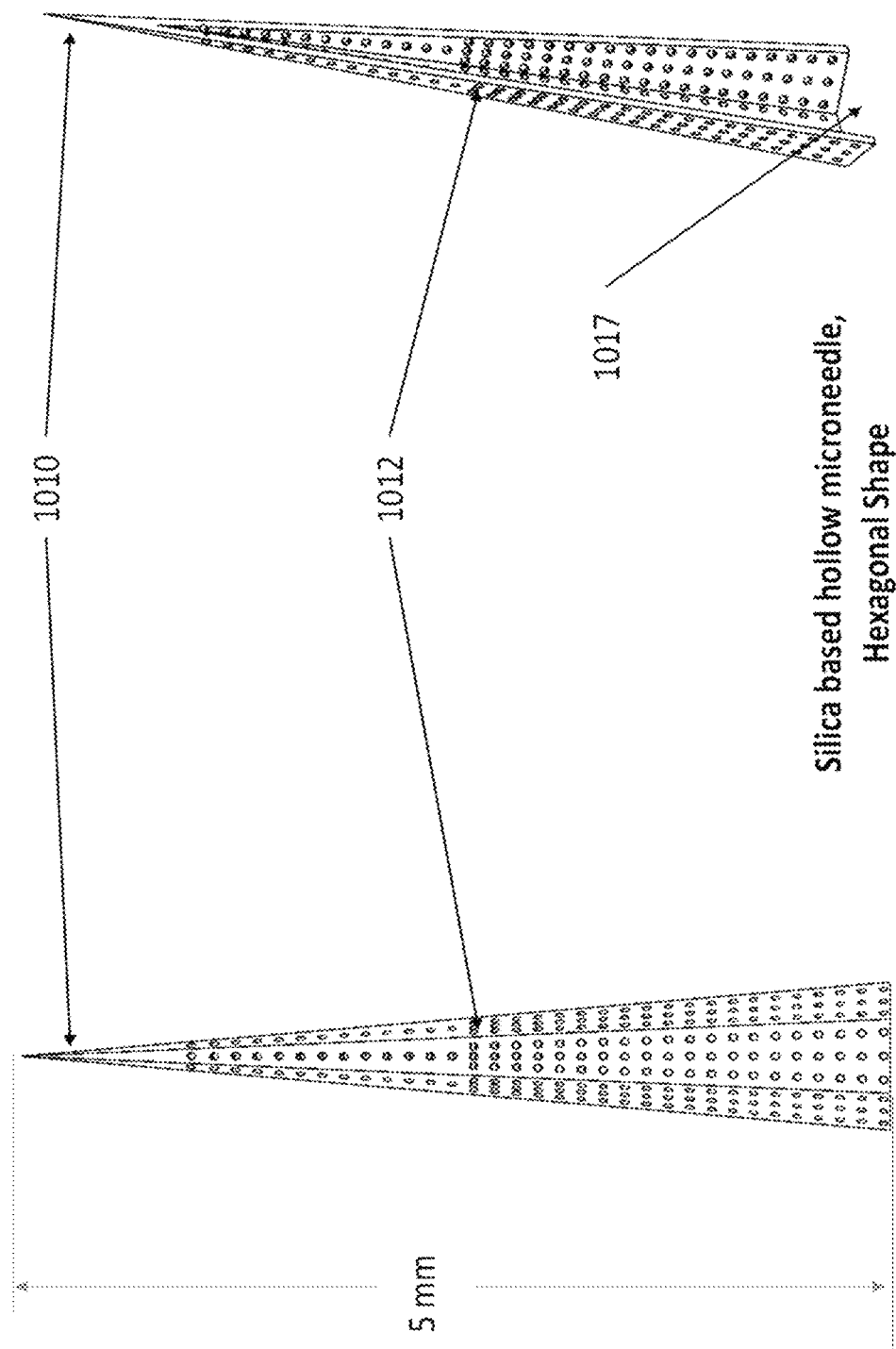
FIG. 10 illustrates a long, hexagonal hollow microneedle.

FIG. 10 illustrates one configuration of a long hollow hexagonal microneedle having a sharp tip (non coated) 1010, a plurality of nanopores (5 to 200 nm diameter, not drawn to the scale) on the surface of hollow microneedle 1012, a hollow structure to store fluid inside for electroporation 1017.

Figure 11:
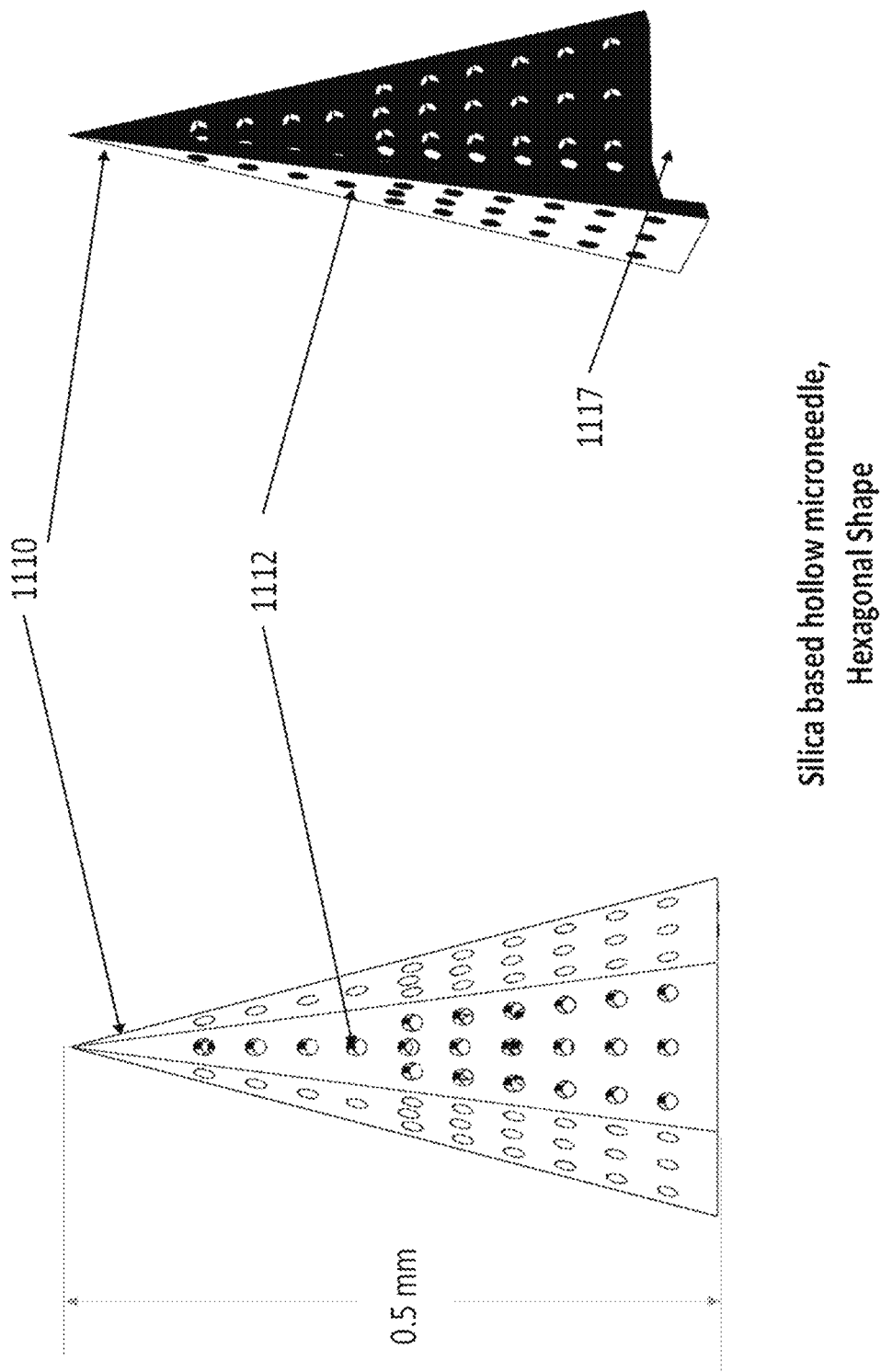
FIG. 11 illustrates a short, hexagonal hollow microneedle.

FIG. 11 illustrates a short configuration of a hollow microneedle having a sharp tip (non coated) 1110, a plurality of nanopores (5 to 200 nm diameter, not drawn to the scale) on the surface of hollow microneedle 1112, and a hollow structure to store fluid inside for electroporation 1117.

Figure 12:
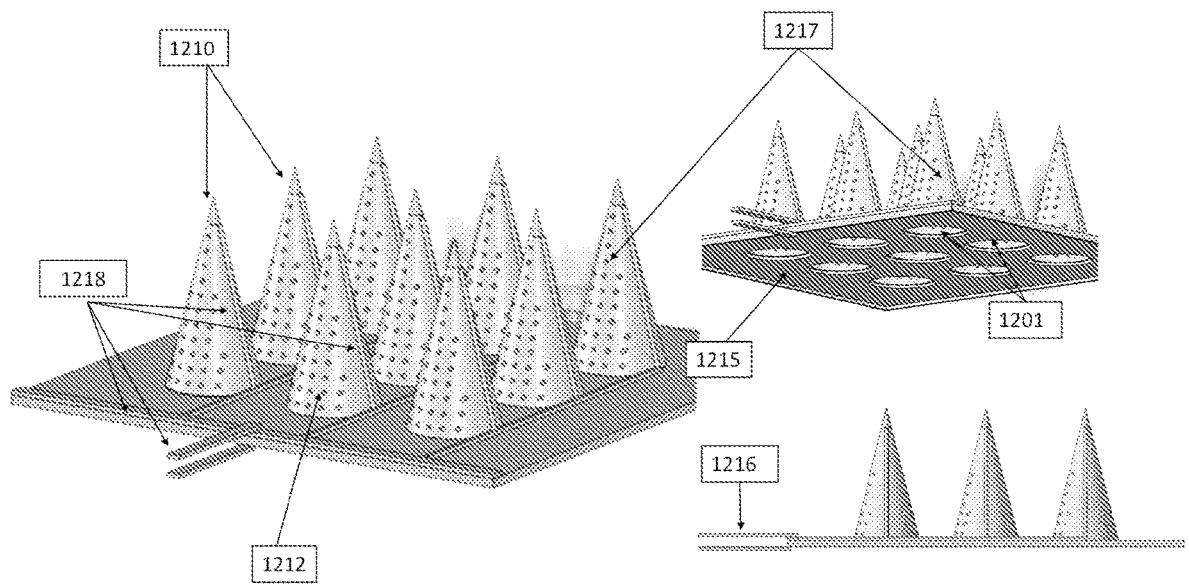
FIG. 12 illustrates an array of cylindrical hollow microneedles with gold tip, and Nanopores on the Surface.
Figure 13:
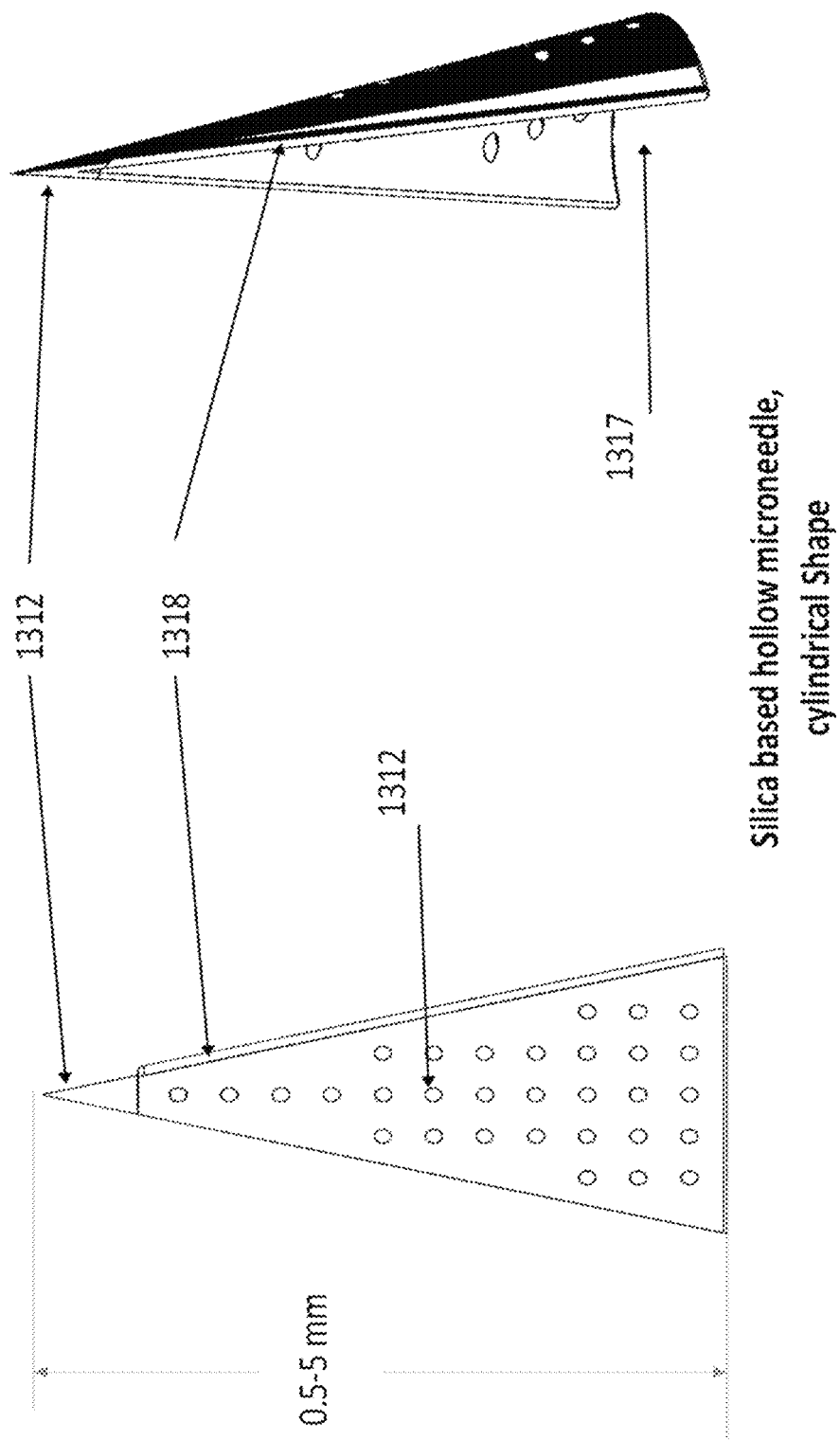
FIG. 13 illustrates a cylindrical hollow microneedle with a gold coated tip.

Another configuration includes cylindrical hollow microneedles with gold coated tips positioned in an array (Silica Based, 0.5-5 mm long, 0.2-1 mm base diameter). FIG. 12 illustrates an example of such an array of microneedles having a gold coated microneedle tip (cathode) 1210, a plurality of nanopores (5 to 200 nm, not drawn to the scale) on the surface of hollow hexagonal microneedles (0.5 to 5 mm long) 1212, a cylindrical microneedle array (0.5-5 mm long, 0.2-1 mm base diameter, hollow inside to store fluid inside) 1217, a gold lining at the edge of the microneedle attached to a common terminal (+/cathode) 1218, a gold coated bottom chamber (anode, fluid reservoir) 1215, and terminals 1216. FIG. 13 illustrates one embodiment of the hollow cylindrical microneedle having a gold coated tip (cathode) 1312, a gold wire at the edge connected between the tip and +terminal 1318, a plurality of nanopores (5-200 nm diameter, not drawn to the scale) on the surface of hollow microneedle 1312, and a hollow structure to store fluid inside for electroporation 1317.

Figure 14:
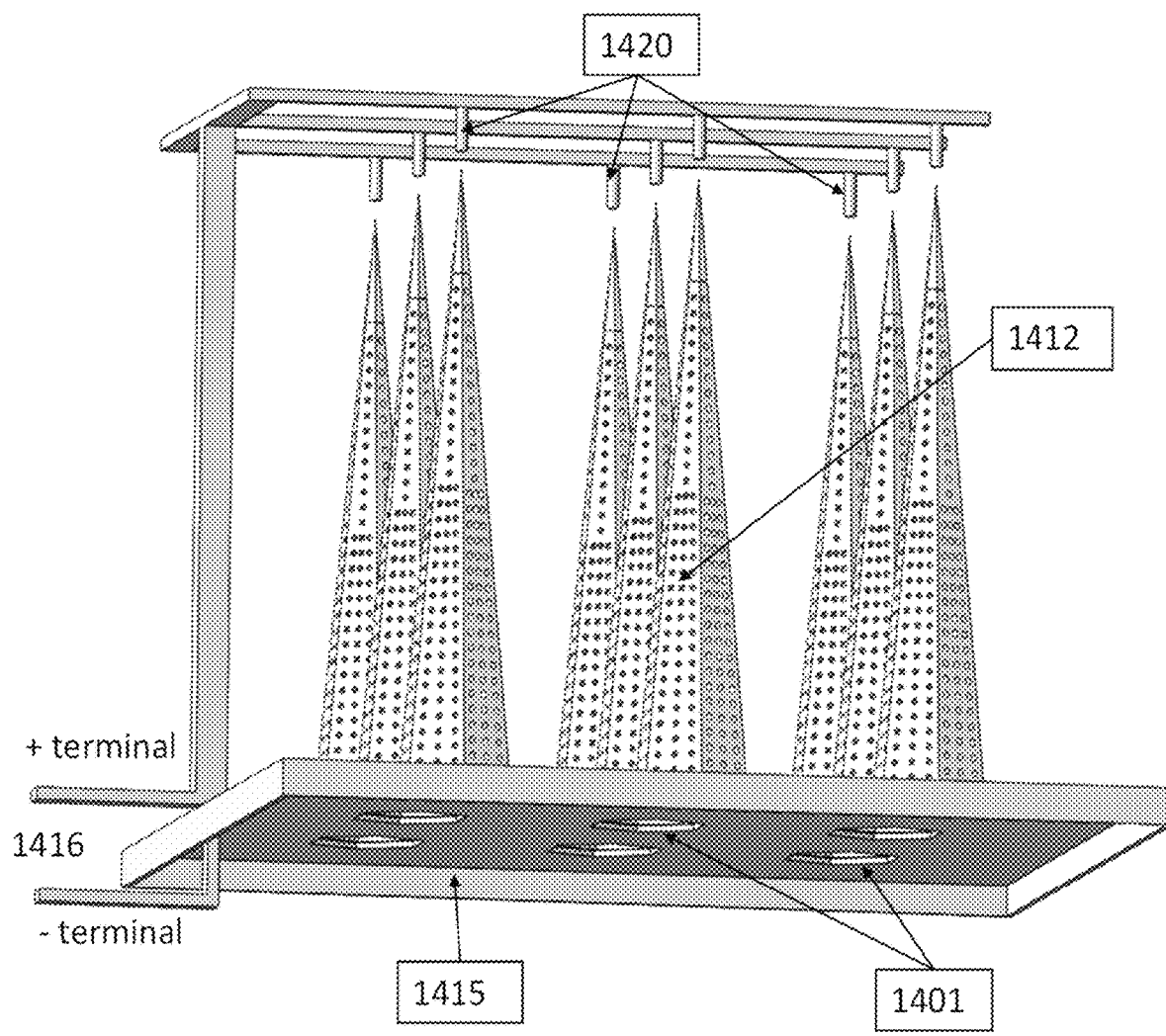
FIG. 14 illustrates an array of hexagonal hollow microneedles with external gold wiring and extended gold fingers above individual microneedle tips, and nanopores on the surface.

An example of another array configuration is provided in FIG. 14. The array is a hexagonal hollow microneedle array with external gold wiring and extended gold fingers above individual microneedle tips. FIG. 14 illustrates a hexagonal microneedle array (5 mm long, hollow inside to store fluid inside) with a gold fingers/external wiring on top of microneedles (cathode) 1420, the microneedles having a plurality of nanopores (5-200 nm, not drawn to the scale) on the surface of hollow hexagonal microneedles (5 mm long) 1412, a gold coated bottom chamber (anode, fluid reservoir) 1415, and a terminals 1416. The microneedles can be long or short microneedled.

Figure 15:
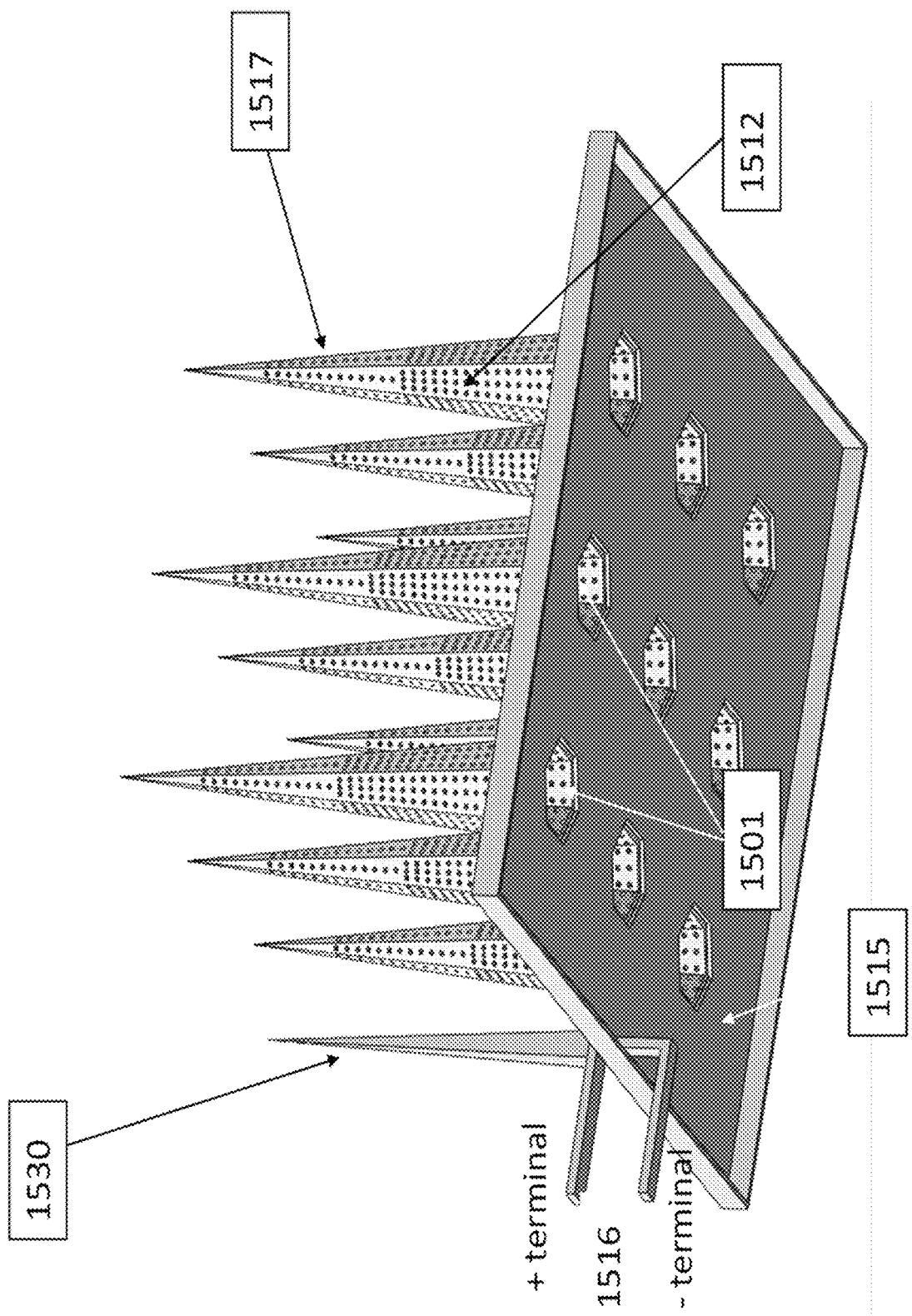
FIG. 15 illustrates an array of hexagonal hollow microneedle with external gold wiring parallel to the microneedles, and nanopores on the surface.

FIG. 15 illustrates one example of a hexagonal hollow microneedle array with external gold wiring parallel to the microneedles. The array having external gold wiring parallel to the microneedles (cathode) 1530, a hexagonal microneedle array (5 mm long, hollow inside to store fluid inside) 1517, a plurality of nanopores (5-200 nm, not drawn to the scale) on the surface of hollow hexagonal microneedles (5 mm long) 1512, a gold coated bottom chamber (anode, fluid reservoir) 1515, and anode and cathode terminals 1516.

Figure 16:
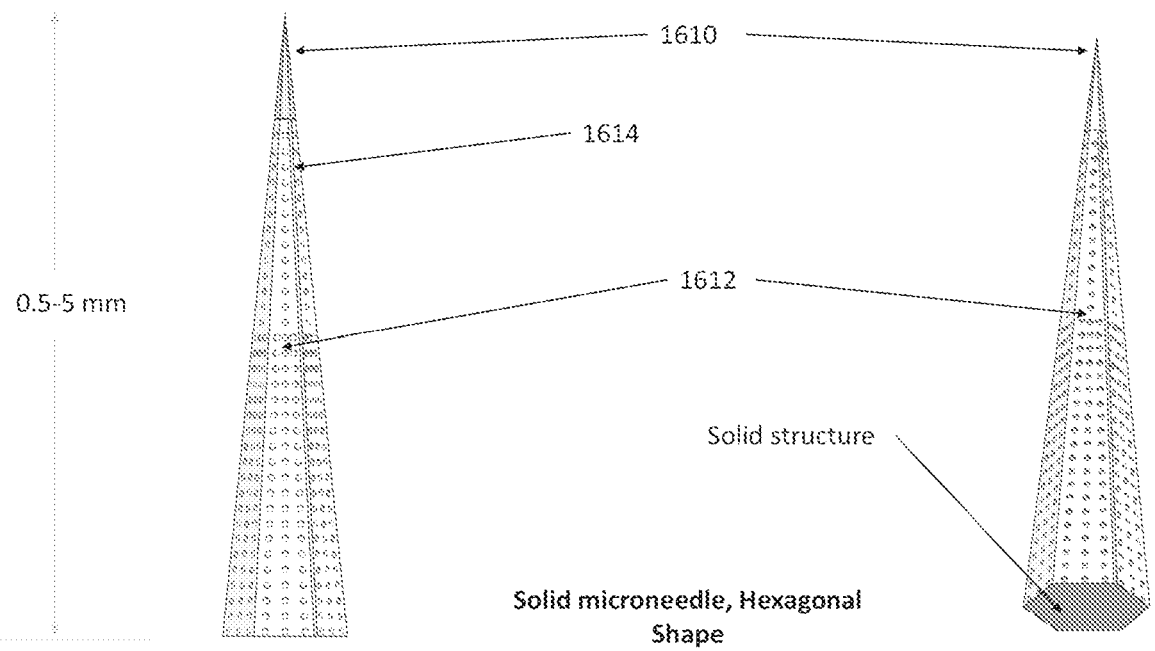
FIG. 16 illustrates a solid hexagonal microneedle.
Figure 17:
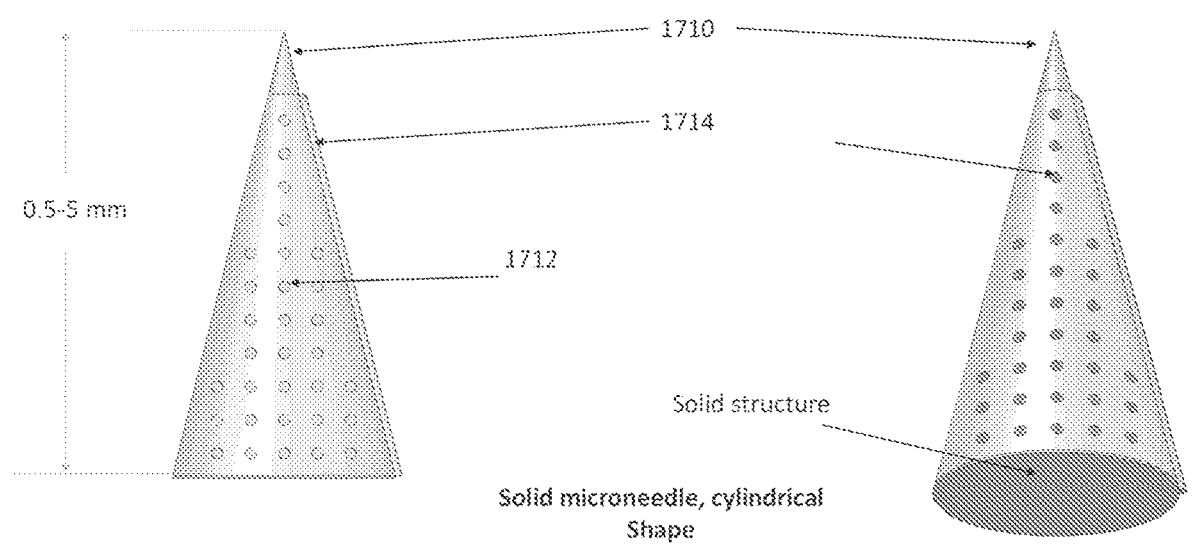
FIG. 17 illustrates a solid cylindrical microneedle.

Other embodiments include a solid microneedle with nanopores (5-200 nm diameter) on the surface that act as a reservoir for fluid. FIG. 16 is an example of a solid hexagonal microneedle having an optional gold coated tip (cathode) 1610, a gold wire at the edge connected between the tip and +terminal 1614, a plurality of nanopores (5-200 nm diameter, not drawn to the scale) on the surface of solid microneedle to store fluid 1612. FIG. 17 is an example of a solid cylindrical microneedle having an optional gold coated, (cathode) 1710, a gold wire at the edge connected between the tip and +terminal 1714, a plurality of nanopores (5-200 nm diameter, not drawn to the scale) on the surface of solid microneedle to store fluid 1712.

The invention claimed is:

1. A device configured for controlled nanoelectroporation and/or electrophoretic insertion of genetic materials into cells, the device comprising:
an array of nanopore microneedles projecting from a base, each nanopore microneedle comprising an elongated shaft 50 to 5000 μm in length from a proximal end connected to the base to a distal sharp tip, the shaft being formed from a wall that defines an interior space inside the shaft, wherein the shaft comprises a plurality of nanopores extending through the wall, the nanopores having a diameter of 5 to 500 nm, wherein each nanopore microneedle is in electrical communication with one or more electrodes.

2. The device of claim 1, wherein the nanopore microneedle tapers to a tip, the tip having a diameter of less than 10 μm.

3. The device of claim 1, wherein the nanopore microneedle has a base diameter of 500 to 1000 μm.

4. The device of claim 1, wherein the nanopore microneedle have polygonal cross section.

5. The device of claim 4, wherein the nanopore microneedle have a hexagonal cross section.

6. The device of claim 5, wherein the hexagonal cross section has a face length of 100 to 1000 μm.

7. The device of claim 1, wherein the nanopores are present at a density of 50,000 to 50,000,000 per square centimeter.

8. The device of claim 1, wherein the nanopore microneedle is a silicon nanopore microneedle.

9. The device of claim 1, wherein the tip of the nanopore microneedle is coated with a conducting material.

10. The device of claim 1, wherein the tip of the nanopore microneedle is coated with gold.

11. The device of claim 1, wherein the base is coated with a conducting material.

12. The device of claim 1, wherein the base is coated with gold.

13. The device of claim 1, wherein the base is configured as an electrode.

14. The device of claim 1, further comprising one or more electrodes that surround an outer surface of the shaft at one or more locations along the length of the shaft, wherein each microneedle further comprises an insulated wire that extends along the shaft to each electrode.

15. The device of claim 1, wherein the base is connected to a first electrode and a second electrode is external to the tip of the nanopore microneedle.

16. A device configured for controlled nanoelectroporation and/or electrophoretic insertion of genetic materials into cells, the device comprising:
an array of nanopore microneedles projecting from a base, each nanopore microneedle comprising an elongated shaft 50 to 5000 μm in length from a proximal end connected to the base to a distal sharp tip, the shaft being formed from a wall that defines an interior space inside the shaft, wherein the shaft comprises a plurality of nanopores extending through the wall, the nanopores having a diameter of 5 to 500 nm, wherein each nanopore microneedle is in electrical communication with one or more electrodes;
one or more electrodes that surround an outer surface of the shaft at one or more locations along the length of the shaft, wherein each microneedle further comprises an insulated wire that extends along the shaft to each electrode; and
the base is connected to a first electrode and a second electrode is external to the tip of the nanopore microneedle.

* * * * *